United States Patent [19]
Van Ness et al.

[11] Patent Number: 5,514,785
[45] Date of Patent: May 7, 1996

[54] SOLID SUPPORTS FOR NUCLEIC ACID HYBRIDIZATION ASSAYS

[75] Inventors: Jeffrey Van Ness, Bothell; Charles R. Petrie, Woodinville; John C. Tabone, Bothell; Nicolaas M. J. Vermeulen, Woodinville, all of Wash.

[73] Assignee: Becton Dickinson and Company, Franklin Lakes, N.J.

[21] Appl. No.: 331,296

[22] Filed: Oct. 28, 1994

Related U.S. Application Data

[63] Continuation of Ser. No. 42,442, Mar. 11, 1993, abandoned, which is a continuation of Ser. No. 522,442, May 11, 1990, abandoned.

[51] Int. Cl.$^6$ .............................. C12Q 1/70; C12Q 1/68; G01N 3/53; G01N 3/566
[52] U.S. Cl. .................. 536/22.1; 435/5; 435/6; 435/7.1; 436/501
[58] Field of Search .................... 435/6, 5, 7.1; 436/501; 536/22.1

[56] References Cited

U.S. PATENT DOCUMENTS

| | | | |
|---|---|---|---|
| 4,921,788 | 5/1990 | Deutsch | 435/6 |
| 4,921,805 | 5/1990 | Gebeyehu et al. | 435/270 |

*Primary Examiner*—W. Gary Jones
*Assistant Examiner*—Dianne Rees
*Attorney, Agent, or Firm*—Townsend and Townsend and Crew

[57] ABSTRACT

Compositions and methods for covalently immobilizing an oligonucleotide onto a polymer-coated bead or similar structure are described. Specifically, the polymer-coated bead or similar structure possesses a large number of activatable moieties, preferably primary and secondary amines. An oligonucleotide is activated with a monofunctional or multifunctional reagent, preferably the homotrifunctional reagent cyanuric chloride. The resultant covalently immobilized oligonucleotides on the beads or similar structures can serve as nucleic acid probes on solid supports, and hybridization assays can be conducted wherein specific target nucleic acids are detected in complex biological samples. The beads or similar structures can be employed free in solution, such as in a microtiter well format; in a flow-through format, such as in a column; or in a dipstick, including a multisite indicator card wherein multiple beads possessing oligonucleotides with different sequences or specificities can be closely aligned whereby a multiplicity of pathogens can be detected in a single biological sample. Additionally, dichlorotriazine oligonucleotides and processes for activating oligonucleotides by treatment with cyanuric chloride are included in the present invention.

11 Claims, 3 Drawing Sheets

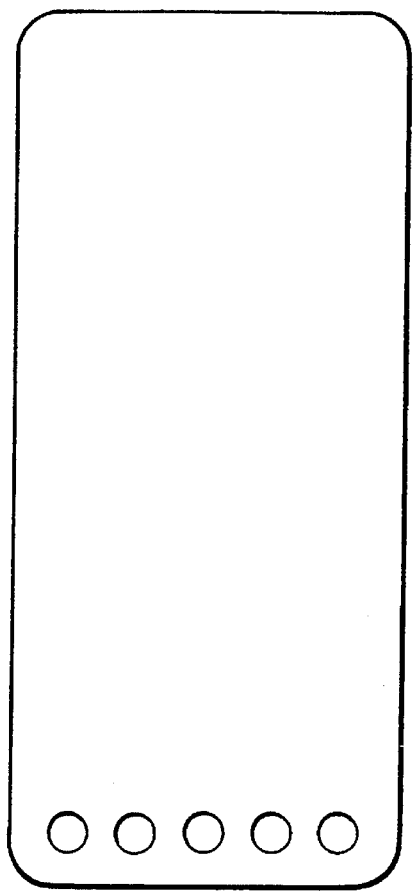
FIG. 1A.  FIG. 1B.
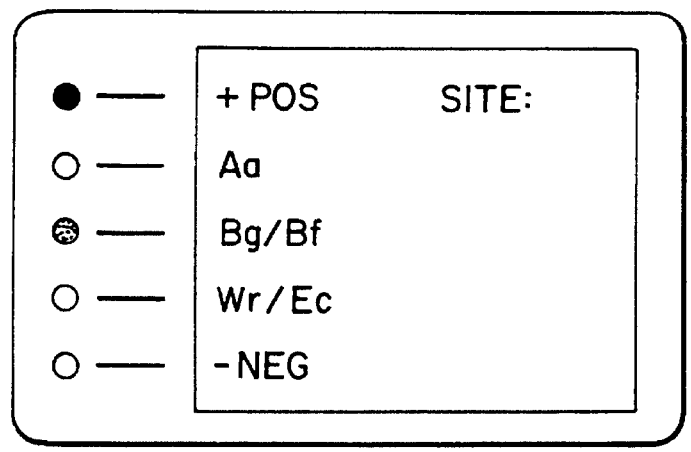
FIG. 2.

SOLID SUPPORTS FOR NUCLEIC ACID HYBRIDIZATION ASSAYS

This is a continuation of application Ser. No. 08/042,442, filed Mar. 11, 1993, now abandoned, which was a continuation of Ser. No. 07/522,442, filed May 11, 1990, now abandoned.

BACKGROUND OF THE INVENTION

The present invention relates generally to the field of nucleic acid hybridization assays for detecting specific polynucleotide sequences and, more particularly, to compositions and methods for covalently attaching activated oligonucleotides to polymer-coated beads serving as solid supports.

Nucleic acid hybridization is a known method for identifying specific sequences of nucleic acids. Hybridization is based upon base pairing between complementary nucleic acid strands. When single stranded nucleic acids are incubated in appropriate buffer solutions, complementary base sequences pair to form double stranded stable molecules. The presence or absence of such pairing may be detected by several different methods described in the art.

Many known hybridization assays involve multiple steps, for example the hybridization technique described by Dunn, et al., Cell 12:23–36 (1977) (incorporated herein by reference), wherein a sandwich-type assay consists of a first hybridization between a "target" nucleic acid and a "capture" nucleic acid probe that has been immobilized on a solid support and a second hybridization between a "signal" nucleic acid probe, typically labeled with a radioactive isotope, and a different region of the immobilized target nucleic acid. The hybridization of the signal probe may then be detected by, for example, autoradiography.

Ranki, et al., U.S. Pat. No. 4,486,539 and U.S. Pat. No. 4,563,419 (both patents incorporated herein by reference), describe sandwich-type assays that first require steps to render nucleic acids single stranded before the single stranded nucleic acids are allowed to hybridize with a nucleic acid affixed to a solid carrier and with a nucleic acid labeled with a radioisotope.

Carrico, et al., U.S. Pat. No. 4,806,546, and Carrico, et al., European Patent Application 86112899.9 (both incorporated herein by reference), have described treatment of a nylon support with an alkylating agent to introduce amidine groups onto the surface of the nylon. The derived nylon surface possesses the capacity to noncovalently bind single stranded nucleic acids. The noncovalently bound nucleic acids are then used as probes to detect specific target nucleic acids in solution.

Hunger, et. al., Analytical Biochemistry 165:45–55 (1987); Hunger, et al., Analytical Biochemistry 156:286–299 (1986); Hunger, et al., European Patent Application 84109485.7 (all incorporated herein by reference), describe the use of cyanuric chloride-activated cellulose paper having immobilized restricted genomic DNA in Southern blot techniques for the detection of subpicogram quantities of complementary DNA. Biagioni, et. al., Analytical Biochemistry 89:616–619 (1978) (incorporated herein by reference), describe a method for the preparation of DNA-cellulose using cyanuric chloride wherein the DNA-cellulose is employed in affinity chromatography procedures.

Herzberg, et al., European Patent Application 0171150 (incorporated herein by reference), describe the use of oligonucleotides immobilized onto solid supports in dipstick assays.

Litman, et al., U.S. Pat. No. 4,391,904 (incorporated herein by reference, describes test strip kits wherein a member of an immunological pair is bonded to a solid surface. Also, Miller, et. al, Clin. Chem. 30:1467–1472 (1984), and Brown, et. al, Clin. Chem. 31:1500–1505 (1985) (both are incorporated herein by reference), describe an analytical test chamber containing cellulose threads coupled to an antibody as a solid matrix that permits multiple test results from a single sample.

SUMMARY OF THE INVENTION

The present invention comprises novel compositions and processes having utility in nucleic acid hybridization assays. According to one aspect of this invention, compositions comprising an activated oligonucleotide, which can be covalently attached to a polymer-coated bead or similar structure are described. Preferably, cyanuric chloride, a homotrifunctional reagent, activates the oligonucleotide. Processes for covalently immobilizing activated oligonucleotides on nylon solid supports are also included herein.

The covalently immobilized oligonucleotides on polymer-coated beads or similar structures can serve as nucleic acid probes, and hybridization assays can be conducted wherein specific target nucleic acids are detected in complex biological samples. The beads can be employed free in solution, such as in a microtiter well format; in a flow-through format, such as in a column; or in a dipstick. Additionally, immobilized oligonucleotides on a polymer-coated bead can be of the same or different nucleic acid sequences.

The bead solid supports of the present invention possess the following advantages over known membrane or bead supports, in which capture nucleic acid sequences are noncovalently attached. First, the capture rate of target nucleic acid sequences is improved 5 to 25-fold, and 100% of the capture nucleic acid sequence is available for hybridization with a complementary sequence; second, the quantity of immobilized capture nucleic acid can be increased approximately 20-fold on an apparent surface area basis; third, greater ease of manufacturing exists; fourth, the bead possesses covalently immobilized, capture nucleic acid sequences (oligonucleotides) and can withstand denaturation temperatures in excess of 90° C. for 10 or more minutes; and, finally, a multisite dipstick can be constructed, leading to miniaturization of a detection device. All of these advantages contribute to greater sensitivities when, for example, a sandwich assay format is used.

Dipsticks are also included in the present invention. These dipsticks comprise a nonporous solid support and a means for attaching the beads or similar structures discussed above. Additionally, multiple beads possessing oligonucleotides with different sequences or specificities can be closely aligned on a multisite dipstick, giving rise to an indicator card that can detect a multiplicity of pathogens in a single biological example, for example, to identify bacterial and viral agents.

The use of beads or similar structures in the dipstick format achieves a significant decrease in nonspecific background levels of signal systems because of the simple pressure fit by which the bead or similar structure is placed in the dipstick, as compared with membrane supports and the like, which necessarily must be sandwiched between two supports or glued or attached in place.

A further understanding of the nature and advantages of the present invention may be realized by reference to the remaining portions of the specification and to the drawings.

BRIEF DESCRIPTION OF THE DRAWINGS

FIG. 1 is a configuration for a dipstick of the present invention;

FIG. 2 is a multisite indicator card that can be used for periodontitis diagnosis.

DETAILED DESCRIPTION OF THE INVENTION

Figure 3A:
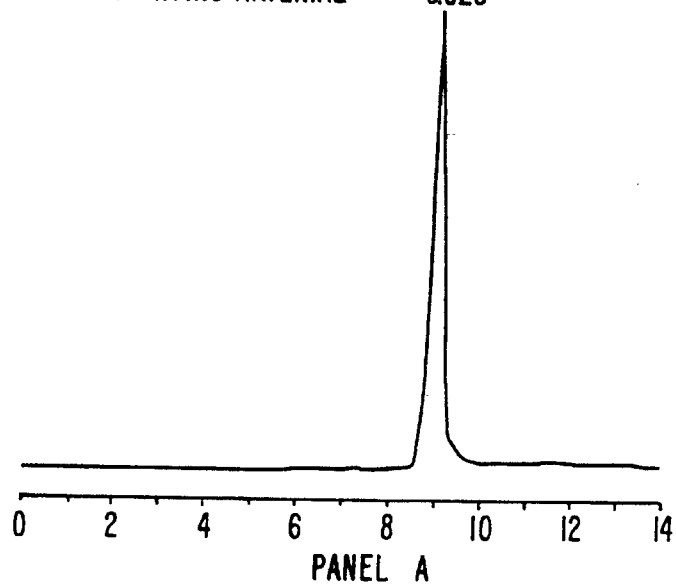
FIG. 3 are high performance liquid chromatography (HPLC) profiles showing that cyanuric chloride reacts selectively with the 5'-tethered amine of an oligonucleotide, and not with sugars or bases thereof.

The present invention includes compositions useful in nucleic acid hybridization assays. These compositions comprise a dichlorotriazine oligonucleotide and other activated oligonucleotides covalently attached to a polymer-coated bead or similar structure.

Additionally, processes for covalently immobilizing an oligonucleotide on a nylon solid support, preferably a bead, are included. In general, these processes comprise the steps of treating a nylon solid support with an alkylating agent; reacting the treated solid support with an amine-containing polymer, whereby the polymer covalently coats the solid support; activating an oligonucleotide with a monofunctional or multifunctional reagent, preferably the homotrifunctional reagent, cyanuric chloride (i.e., 2,4,6-trichlorotriazine); conjugating the activated oligonucleotide and the polymer-coated solid support. The unreacted amines are then blocked by acylatation to impart the proper surface charge to the solid support surface.

The term "solid support" refers to any surface that is transferable from solution to solution or forms a structure for conducting oligonucleotide-based assays, and includes beads, membranes, microtiter wells, strings, plastic strips, or any surface onto which nucleic acid probes may be immobilized.

As used herein, "bead" encompasses any type of solid or hollow sphere, ball, bearing, cylinder, or other similar configuration composed of plastic, ceramic, metal, or polymeric material onto which a nucleic acid can be covalently immobilized. As such, the term also includes nylon string or strings. Preferably, a nylon bead that is spherical in shape is employed in the present compositions, and a preferred diameter range for such beads is from about 0.01 inch to about 0.5 inch, more preferably from about 0.06 inch to about 0.09 inch (corresponding to commercially available 3/32 inch nylon beads), and most preferably about 0.09 inch (corresponding to commercially available 3/32 inch nylon beads). Additionally, it is preferred that the nylon beads are unpolished or, if polished, roughened before treating with an alkylating agent.

In the present invention, a nylon bead or beads, or any composition or structure of nylon, is first derived (prepared) by treating the bead with an alkylating agent. Alkylating agents used in this manner react with amides present in the nylon to form a reactive imidate ester.

Preferred alkylating agents include, but are not limited to, dialkyl sulfates, alkyl triflates, alkyldiphenyl sulfonium salts, alkyl perchlorates, and, preferably, trialkyloxonium salts. The latter includes the lower alkyl salts, trimethyloxonium and triethyloxonium salts. The salt counterion can be selected from the group consisting of hexachloroantimonate, hexafluorophosphate, and tetrafluoroborate, with the last named counterion being preferred; however, other salt counterions can also be used and will be apparent to one skilled in the relevant art.

The selection of a solvent for the alkylating agent is important for the present invention. A solvent should be employed that does not dissolve or render tacky nylon during the alkylation. Non-nucleophilic organic solvents, such as dichloromethane, dimethylsulfoxide, tetrahydofuran, N-methyl-pyrrolidone, and others are appropriate solvents. In particular, N-methyl-pyrrolidone is preferred.

The resulting imidate esters on the bead surface are then reacted under suitable conditions with an amine-containing polymer, whereby amidine residues are formed. Any primary or secondary amine-containing polymer can be employed to form amidine residues, thus covalently immobilizing the polymer onto the surface of the bead. Poly(ethyleneimine), polyallylamine, and polyvinylamine are preferred examples. The preferred solvent used to dissolve the polymer during the conjugation of the polymer to the activated nylon bead is N-methyl-pyrrolidone.

Nylon can also be partially hydrolyzed to yield reactive amine or carboxyl groups that can be reactive with amine- or carboxyl-containing polymers. Similarly, any carboxyl moieties coating the surface of a solid support can be coated with amine-containing polymers using similar chemistries described above.

In addition, any other polymer capable of being derived with any primary or secondary aliphatic or aromatic amine is suitable for the present invention. The units of such a polymer are joined together by direct polymerization process bonding or by coupling agent linking. Direct polymerization produces interbonding of available chemical groups or backbone moieties in adjacent units. For example, oxidative enzymes can be used to polymerize monomer units by oxidative cross-linking. Alternatively, a coupling agent, derived from a bifunctional or multifunctional organic cross-linking agent, can bond with the appropriate chemical group or backbone moiety of the units. In this context the term "coupling agent" denotes the linkage group after bonding and the term "cross-linking reagent" denotes the linkage compound before bonding.

The cross-linking reagent has generic formula:

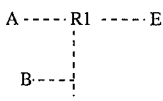

wherein reactive groups A, B, and E are independently selected from the group consisting of hydrogen, a carboxylic acid group, an acid halide, an activated ester, a mixed anhydride, an iminoester, a primary amine, an aldehyde group, an α-halo methylcarbonyl group, a hydrazine group, an acyl hydrazide group, an azide group, and an N-maleimide group, wherein at least two of A, B, and E are other than hydrogen. $R^1$ is an aliphatic group of at least two carbons or an aromatic or heterocycle group of at least six carbons.

Multifunctional cross-linking reagents, with more than three reactive groups that are similar to A, B, and E are also within the scope of the present invention. These additional reactive groups will be independently selected from the foregoing definitions of A, B, and E.

Choice of the reactive groups will depend upon the selection of the chemical groups or backbone moieties of the polymer units (monomeric units) that are to be linked. Each type of chemical group or backbone moiety will react with the appropriate reactive group or groups. For example, an amine group will react with a carboxylic acid group, an acid halide, an activated ester, a mixed anhydride, an acyl imidazolide, an N-(carbonyloxy)imide group, an iminoester, or an aldehyde group. An oxidized 1,2-diol group (a dialdehyde) will react with a primary amine, a hydrazine group, an azide, or an acyl hydrazide group. A carbonyl group will react with a primary amine, a hydrazine group, or an acyl hydrazide group. A mercaptan group will react with a carboxylic acid group, an acid halide, an activated ester, a mixed anhydride, an acyl imidazolide, or an N-(carbonyloxy)imide. A carbon-hydrogen bond will react with an azide (nitrene). The solid supports are thus coated with the selected polymer, including multifunctional polymers, that contains a large number of activatable primary and secondary amines.

The table below illustrates, but does not limit, the types of reactions that may be employed in the present invention to covalently attach, either directly or through a spacer arm, a polymer to a solid support. As can be seen, although amine-containing polymers are preferred, other polymers containing thiol or carboxyl groups can be employed as well.

| Bead functionality: | Polymer functionality: | Coupling reagent: |
| --- | --- | --- |
| Amine | Amine | Cyanuric chloride |
| Amine | —COO⁻ | Carbodiimide |
| Amine | —SH | Heterobifunctional |
| —COO⁻ | Amine | Carbodiimide |
| —OH | Amine | Cyanuric chloride |

The polymer-coated solid supports are then conjugated with activated oligonucleotides using similar or identical chemistries to those described above. As used herein, oligonucleotides refer to short nucleic acid sequences that are approximately 16 to 100 bases in length. Such oligonucleotides can be used as capture probes in hybridization assays and are preferably chemically synthesized using commercially available methods and equipment. For example, the solid phase phosphoramidite method can be used to produce short probes of between 15 and 50 bases having a molecular weight of less than 16,000 daltons. For the synthesis of oligonucleotides, see Caruthers, et al., Cold Spring Harbour Symp. Quant. Biol., 47:411–418 (1982); Adams, et al., J. Am. Chem. Soc., 105:661 (1983) (both are incorporated herein by reference).

When synthesizing an oligonucleotide probe for a specific target nucleic acid, the choice of nucleotide sequence will determine the specificity of the test. For example, by comparing DNA sequences from several bacterial isolates, one can select a sequence for bacterial detection that is either type-specific or genus-specific. Comparisons of DNA regions and sequences can be achieved using commercially available computer programs.

The preferred capture oligonucleotides for use in the present invention are synthetic oligonucleotides from about 20 to about 100 bases in length. A spacer (linker) arm, i.e., a chemical moiety that extends or links other chemical groups, and preferably is a carbon chain containing from about 2 to about 12 carbon atoms, more preferably about 6 carbon atoms, containing a blocked amine group can be coupled during synthesis using conventional chemistry to the 5'-hydroxyl group of an oligonucleotide. A primary amine is the preferred group for attachment to monofunctional or multifunctional reagents, and its attachment via a hexyl arm is preferred. The reagents for the attachment of primary spacer arms terminating in a primary amine are commercially available. Starting materials suitable for use in the present invention are described in PCT 86/01290; Nucl. Acids Res. 15:3131 (1987); Nucl. Acids Res. 15:2891 (1987); and Nucl. Acids Res. 14:7985 (1986) (all incorporated herein by reference).

Preferably, an oligonucleotide possessing a 5'-terminal structure such as

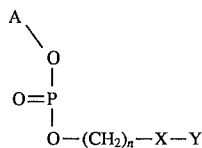

is employed wherein, as a spacer arm, n is 2–12 inclusive, preferably 6; X is —NH— or —NHC:O(CH$_2$)$_m$NH—, preferably —NH—; wherein m is 2–12, inclusive; Y is a 4,6-dichlorotriazine (preferred) or thiol (sulfhydryl) reactive moiety; and A is an oligonucleotide, ranging from between about 9–50 bases, preferably between about 15–30 bases, with only the 5'-hydroxyl requiring modification for attachment.

Alternatively, an oligonucleotide can be modified at the 3'-end with a spacer arm containing a blocked amine group. This can be accomplished by conducting DNA synthesis on a solid support containing a conjugated ribonucleotide. After removal from the solid support, a DNA oligonucleotide is obtained that contains a single 3'-terminal ribonucleotide. This can be modified with a spacer arm containing a nucleophilic amine by, for example, oxidizing the ribonucleotide cis-glycol with periodate; treating oligonucleotide so modified with, for example, butane diamine to form a Schiff base; and treating with sodium borohydride or cyanoborohydride to form a stable reduced Schiff base derivative in which one of the amines is left free for subsequent conjugation.

The selected oligonucleotides are then activated with a monofunctional or multifunctional reagent. Activated oligonucleotides refer in general to oligonucleotides that have been reacted with a chemical compound and rendered chemically active. As used herein, activatable refers to the potential to become chemically reactive. Multifunctional reagents include, but are not limited to, homotrifunctional, heterotrifunctional, homobifunctional, and heterobifunctional reagents.

Activated oligonucleotides may be linked to polymer-coated solid supports according to the following chemistries. In general, there are two modes by which the oligonucleotide can be covalently attached to the polymer at this point. An amine-tailed oligonucleotide can be activated with a monofunctional or multifunctional reagent, for example cyanuric chloride whereby an alkylamino dichlorotriazine is formed, which is then reactive toward the amine-containing polymer. Alternatively, the polymer on the surface of the bead can be activated with a reagent, preferably the homotrifunctional reagent cyanuric chloride, which is then reactive toward the amine-tailed or amine-derived oligonucleotide.

Although cyanuric chloride, a homotrifunctional reagent is preferred, other reagents can be used. For example, N-succinimidyl-4-(iodoacetamido)-benzoate (SIAB) is a heterobifunctional reagent, and disuccinimidyl suberate is a homobifunctional reagent. If carboxyl groups are involved, the heterobifunctional reagent, 1-ethyl-3-(dimethylaminopropyl)carbodiimide can be used. Other similar monofunctional and multifunctional (heteromultifunctional and homomultifunctional) reagents are included for use in processes of the present invention.

The chemistries employed in the present invention result in the selective activation of an amino group on an oligonucleotide, without modification of any of the purine and pyrimidine bases of the oligonucleotide, as demonstrated in Example 1 below. The placement of the amine-containing polymer on the bead surface and the covalent immobilization of an activated capture oligonucleotide onto such a surface increases the rate or extent of capture of target nucleic acid 5 to 25-fold compared with diamine compounds, for example, hexanediamine. Additionally, the nonspecific binding of biological material on the surface of the bead is substantially reduced.

The preferred chemistry employs cyanuric chloride (i.e., 2,4,6-trichlorotriazine). The chemistry of the cyanuric chloride reaction is as follows.

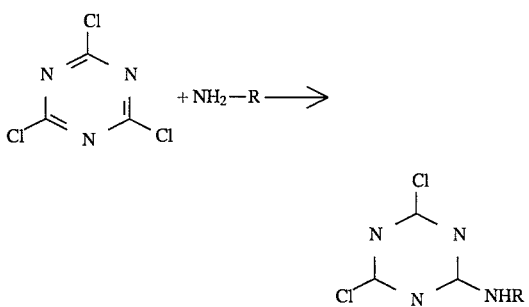

wherein R is an oligonucleotide and preferably is of the structure depicted for a 5'-amino hexyl oligonucleotide.

Oligonucleotides possessing a 5'- or 3'-tethered (via a hexyl arm) nucleophilic amine moiety (or internal aminoalkyl groups substituted on pyrimidine or purine bases) are reacted with an excess, preferably from about 50 to about 200-fold, more preferably 125-fold, of recrystallized cyanuric chloride at, preferably, 15°–50° C., more preferably at 19°–25° C., in a part organic solvent for a preferred time period from about 30 minutes to about 6 hours, more preferably from about 1 to about 2 hours.

Once an oligonucleotide has been activated with cyanuric chloride, it can be covalently linked to molecules that contain appropriately disposed nucleophiles such as thiols, hydroxyls, or amines. More specifically, in addition to covalent attachments with solid supports discussed below, dichlorotriazine oligonucleotides can serve as electrophiles for covalent attachment to many compositions including, but not limited to: proteins, such as enzymes, antibodies, lectins, and protein carriers used to raise antibodies; nucleophile-derived oligonucleotides, such as 5'- or 3'-aminohexyl-tailed oligonucleotides; nucleophile-containing polymers, such as poly(ethyleneimine), polyallylamine, and polyvinylamine; low molecular weight compounds containing nucleophiles, such as radioactive labels, chemiluminescent labels, fluorescent labels, colored labeles, and immunogenic labels; etc. Dichlorotriazine oligonucleotides are included in the present invention, as are processes for activating oligonucleotides with cyanuric chloride to form dichlorotriazine oligonucleotides as discussed below.

The unreacted cyanuric chloride can be removed by exclusion chromatography or ultrafiltration, and the bead and derived oligonucleotide conjugated wherein they are mixed together and incubated at, preferably 20° to 50° C. for 1 to 24 hours. The residual (unreacted) amines on the bead surface can be blocked (capped) with an agent, such as succinic anhydride, preferably in N-methyl pyrrolidone in the presence of an appropriate base such as sodium borate, to render the surface compatible (negatively charged) for nucleic acid hybridization. Such blocking of amines occurs through an acylating reaction or reaction of amines with an activated ester, resulting in a nonactivatable moiety. It should be noted that the ability exists for the bead surface to be chemically derived such that a positive, negative, or neutral charge can be placed on the bead.

In addition, 4,6-dichlorotriazine moieties can be replaced with thiol reactive substituents and, preferably, spacer arms are present. The preferred spacer arms are derived from thiol reactive substituents linked to a 5'-tethered nucleophilic amine and are of the same formula as listed above with the exception that Y in the formula above is a thiol reactive moiety. A preferred thiol reactive moiety has a reactive group of either an α halo-acyl or an β-unsaturated carbonyl. The most preferred thiol reactive moieties are selected from the group consisting of haloacetamidobenzoyl and 4-(N-maleimidomethyl)- cyclohexane-1-carbonyl.

A polymeric structure as described above wherein the polymeric structure is derived with thiol (sulfhydryl) containing moieties can be used in the present invention. The actual structure of the thiol containing moieties is noncritical as long as the thiol group or groups are available to react with thiol reactant moieties. The thiol chemistries in this instance are replacements for cyanuric chloride chemistries.

The present invention also includes dipsticks having utility in nucleic acid hybridizations and comprising a nonporous solid support and a means for attaching a bead. Nonporous solid supports are known in the art, and the present invention is concerned with attaching a bead to a dipstick. An example of bead attachment is the presence of a perforation or perforations (or a depression or depressions) in the dipstick wherein beads can be attached. Preferably, perforations are employed and the beads are attached through a pressure fit with the circumference of the hole. Such a pressure fit can occur if, for example, the circumference of the perforation (or depression) is slightly less than the circumference of the bead so that the bead is pressed in place.

Preferred beads are as listed above, and may be covalently attached, either directly or through a spacer arm, to activated oligonucleotides of the same or different sequence per a given bead, as also described above.

The dipstick can contain more than one bead, preferably from about two to ten, each in their own hole, and more preferably, situated in a row along one edge of the dipstick. Such a dipstick can function as an indicator card, wherein multiple beads covalently attached to oligonucleotides with different sequences or specificities can be closely aligned on a multisite dipstick, which can detect a multiplicity of pathogens in a single biological sample. A particular bead may contain oligonucleotides with more than one nucleic acid sequence, for example, sequences from related organisms, or a bead may only contain oligonucleotides with a given nucleic acid sequence.

Numerous organisms and cell types, including pathogenic and nonpathogenic entitites, can be detected in this manner from a variety of biological sample types. Organisms include bacteria and viruses as well as other microorganisms, and cell types include, for example, those involved in inherited diseases and metabolic disorders. Many other detection applications will be apparent to one of ordinary skill in the art. For example, purported causative bacterial agents of periodontitis, such as Actinobacillus actinomycetemcomitans, Bacteroides gingivalis, Bacteroides forsythus, Bacteroides intermedius, Eikenella corrodens, Fusobacterum nucleatum, and Wolinella recta, can be identified.

It will be obvious to one of ordinary skill in the art that, although the present invention is described in terms of nucleic acid hybridization assays, many other uses for these dipsticks are possible. Any member of a ligand pair can be attached to beads in the dipstick, and the dipstick can then be used to identify the corresponding ligand member. For example, antigens or antibodies could be attached to beads, as described above, in a dipstick and then their corresponding antibodies or antigens, respectively, could be identified. In a similar manner, biotin and streptavidin can be used.

Furthermore, the present invention also includes processes for nucleic acid detection wherein a composition comprising a polymer-coated bead, preferably having activatable amine groups, covalently attached to an activated oligonucleotide is contacted with a target nucleic acid under suitable conditions for hybridization and the hybridized product is detected. Such processes can occur in a microtiter well, a flow-through column, and using a dipstick, as described above.

Target nucleic acid is usually a polynucleotide with an average length from about 20 to about 20,000 bases or nucleotides in length. Suitable conditions for hybridization refer to stringent conditions wherein base-pairing mismatching does not occur and the hybridized product is perfectly base-paired.

The particular hybridization technique is not essential to the invention and one of ordinary skill in the art will appreciate the variety of such techniques. Hybridization techniques are generally described in Hames, B. D., et al. (ed.), Nucleic Acid Hybridization, A Practical Approach, IRL Press, New York (1985). As improvements are made in hybridization techniques, they can readily be applied to the present invention.

Sandwich assays can be preferably employed in the present processes wherein the target nucleic acid to be detected is either extracted or in the original sample and is sequestered (captured) on a solid support, such as beads, by hybridization (i.e., pairing of complementary bases) to capture oligonucleotide probes covalently immobilized on the surface of the support. The captured nucleic acid is then hybridized to a signal oligonucleotide probe or, alternatively, this step can be performed simultaneously with the capture of the target by including the signal probe within, for example, the hybridization solution. The signal probe can be, for example, labeled with biotin. This results in a "sandwich" of the capture oligonucleotide probe:target nucleic acid:signal oligonucleotide probe, constituting a sandwich assay. The solid support is then washed to remove unhybridized material, and the labeled nucleic acid is then measured in accordance with detectable characteristics of the label.

Various labels can be used in hybridization assays benefiting from this invention. Such labels act as reporter groups for detecting duplex formation between the target sequence and its complementary signal sequence. A reporter group as used herein is a group having a physical or chemical characteristic that can be measured or detected. Detectability may be provided by such characteristics as color change, luminescence, fluorescence, or radioactivity. Or, it may be provided by the ability of the reporter group to serve as a ligand recognition site. Any haptenic or antigenic compound can be used in combination with a suitably labeled antibody.

Enzymes of interest as reporter groups will primarily be hydrolases, particularly phosphotases, esterases, ureases, and glycosidases, or oxidoreductases, particularly peroxidases. Fluorescent compounds include fluorescein and its derivatives, rhodamine and its derivatives, dansyl, umbelliferone, etc. Chemiluminescers include luciferin, luminol, and oxetanediones. The above list is not complete, and the choice of label depends on sensitivity required, ease of conjugation with the probe, stability requirements, and available instrumentation.

It is to be understood that the above description and the following experimental section are intended to be illustrative and not restrictive. Many variations and applications will be readily apparent to one of ordinary skill in the art upon reviewing this disclosure.

In the experimental section below, Example 1 describes the selective activation of aminohexyl-tailed oligonucleotides with cyanuric chloride. Example 2 describes the comparison of nylon beads derived with various diamines and poly(ethyleneimine) in terms of the ability of the solid support to promote hybridization. Example 3 describes the use of oligonucleotide derived nylon beads in a sandwich assay in which hybridization is detected using an insoluble colorimetric substrate. Example 4 describes the use of oligonucleotide derived nylon beads in a sandwich assay in which target is detected in complex biological samples.

Example 5 describes the use of oligonucleotide derived nylon beads in a sandwich in which target is detected by chemiluminescence. Example 6 describes the use of oligonucleotide derived nylon beads in a sandwich in which target is detected by a fluorescence-based signal system. Example 7 describes the use of oligonucleotide derived nylon beads immobilized in a dipstick to form a multi-site detection panel or card.

The following Materials and Methods section pertains to the above-summarized Examples 1–7.

Materials

APB buffer is 0.18M NaCl, 0.05M Tris-HCl pH=7.6, 5 mM EDTA, and 0.5% Tween 20.

TMNZ buffer is 0.05M Tris pH=9.5, 1 mM $MgCl_2$, 0.5 mM $ZnCl_2$.

FW (filter wash) is 0.09M sodium chloride, 50 mM Tris pH 7.6, 25 mM EDTA.

SDS/FW is FW and 0.1% sodium dodecyl sulfate (SDS).

HRP (horseradish peroxidase) substrate solution is 0.1M sodium citrate pH 6.5, 0.2M NaPhosphate, 0.5 mg/ml.

4-methoxy-1-naphthol, 0.02 mg/ml 3-methyl-2-benzothiazolinone hydrazone and 0.0135% hydrogen peroxide.

AP (alkaline phosphatase) substrate solution is 1 mM 5-bromo-4-chloroindoyl-3-phosphate, 1 mM nitroBlue tetrazolium, and 0.01% Tween 20 in TMNZ.

Lysis and hybridization solution is 3M guanidinium thiocyanate, 2% N-lauroylsarcosine (sarcosyl), 50 mM Tris pH 7.6, 25 mM EDTA.

CAP buffer is 0.1M NaCitrate pH=6.5 and 0.2M NaPhosphate.

The fluorescent substrate for alkaline phosphatase is 0.02 mM 4-methyl-umbelliferone phosphate, 0.05M Tris pH=9.5, 1 mM $MgCl_2$, 0.5 mM $ZnCl_2$.

The chemiluminescent substrate for alkaline phosphatase was a pre-prepared cocktail from Lumigen, Inc. (Detroit, Mich.).

Oligonucleotide sequences:
Bg1: 5'-XCAATACTCGTATCGCCCGTTATTC-3'
Aa004: 5'-XACCCATCTCTGACTTCTTCTTCGG-3'
Bg016: 5'-XTACTCGTATCGCCCGTTATTCCCG-3'

Ek007: 5'-XAAAAGTGGTATTAGCACTTCCCTT-3'
PA005: 5'-XGACATACCTTCCACCATCTGCAAG-3'
PA505: 5'-XCTTGCAGATGGTGGAAGGTATCTC-3'
UP9A: 5'-XCTGCTGCCTCCCGTAGGAGT-3'
UP007: 5'-XGTATTACCGCGGCTGCTG-3'

Poly(ethyleneimine) was purchased from Polysciences (Warrington, Pa.).

Burnished or unpolished nylon beads were purchased from Precision Ball Company (Chicago, Ill.) and The Hoover Group (Sault St. Marie, Mich.)

Triethyloxonium tetrafluoroborate, hexanediamine, phenylenediamine, succinic anhydride and N-methyl-pyrrolidinone (N-methyl-pyrrolidone, m-pyrol) were purchased from Aldrich Chemical (Milwaukee, Ill.).

N-succinimidyl 4-(iodoacetamido)-benzoate (SIAB) and Tween 20 was purchased from Pierce (Rockford, Ill.).

Guanidium isothioscyanate (GuSCN) was purchased form Kodak (Rochester, N.Y.).

Nylon membrane, Nytran™, was purchased from Scheicher & Schuell, (Keene, N.H.).

The di- and triamines EDR-148, ED-400, ED-6000, and T-3000 were a gift from Texaco Chemical Company, (Houston, Tex.).

Procedures

Oligonucleotide synthesis:

Oligonucleotides complementary to regions conserved or hypervariable regions of the 16S-ribosomal RNA of either Actinobacillus actinomycetemcomitans (Aa), Bacteroides gingivalis (Bg), Bacteroides intermedius (Bi), Eikenella corrodens (Ek), Fusobacterium nucleatum (Fn), or Wolinella recta (Wr) were synthesized using phosphoramidite chemistry on either an ABI 380B or a Milligen 7500 automated DNA synthesizer. The oligonucleotides were prepared using the standard phosphoramidite chemistry supplied by the vendor or the H-phosphonate chemistry. Appropriately blocked dA, dG, dC, and T phosphoramidites are commercially available in these forms, and synthetic nucleosides may readily be converted to the appropriate form. Oligonucleotides were purified by adaptations of standard methods. Oligonucleotides with 5'-trityl groups were chromatographed on HPLC using a 12 μm, 300 Å Rainin (Woburn, Mass.) Dynamax C-8 4.2×250 mm reverse phase column using a gradient of 15% to 55% MeCN in 0.1N $Et_3NH^+$ $OAc^-$, pH 7.0, over 20 min. When detritylation was performed, the oligonucleotides were further purified by gel exclusion chromatography. Analytical checks for the quality of the oligonucleotides were conducted with a Toso-Haas DEAE-NPR column at alkaline pH and by polyacrylamide gel electrophoresis (PAGE).

Preparation of the polymer-coated nylon bead:

25,000 3/32 inch diameter unpolished nylon beads were placed in a flask containing 1800 ml of 100% anhydrous n-methyl-pyrrolidinone and mixed for 5 minutes at ambient temperature. 200 ml of 1 molar triethyloxonium tetrafluoroborate in dichloromethane was added and the mixture was stirred for 30 minutes at ambient temperature. The beads were then decanted and washed quickly with 4,500 ml changes of 100% n-methyl-pyrrolidinone. The beads were then transferred to a solution consisting of 3% w/v 10,000 MW poly(ethyleneimine), prepared from a 30% aqueous solution of poly(ethyleneimine), in n-methyl-pyrrolidone and stirred for 12 to 24 hours at ambient temperature. The beads were washed with 2000 ml n-methyl-pyrrolidone, 1000 ml SDS/FW and finally 10×2 liter stilled water. The beads were then dried under a high vacuum for 4 to 5 hours without the use of heat. The amine content of the beads was determined by reaction with picyrlsulfonic acid.

Preparation of cyanuric chloride-derived oligonucleotides:

10 to 1000 μg of 5'-amine-linked oligonucleotide were reacted with an excess of recrystallized cyanuric chloride in 10% n-methyl-pyrrolidone in an alkaline buffer (pH 8.3 to 8.5, preferably) at 19° to 25° C. for 30 to 120 minutes. The final reaction conditions consisted of 0.15M sodium borate at pH 8.3, 2 mg/ml recrystallized cyanuric chloride and 500 ug/ml respective aminohexyl oligonucleotide. The unreacted cyanuric chloride was removed by size exclusion chromatography on a G-50 Sephadex™ (Pharmacia, Uppsala, Sweden) column.

Preparation of iodoacetamidobenzoylated oligonucleotides:

100 to 1000 μg of 5'-amine-linked oligonucleotide (UP9A) oligonucleotide were reacted with an excess of N-succinimidyl 4-(iodoacetamido)-benzoate (SIAB) in an alkaline (pH 8.0 preferably) buffer at 18° to 25° C. for 30 to 120 minutes. The unreacted SIAB is removed by size exclusion chromatography on G-50 Sephadex™ (Pharmacia, Uppsala, Sweden).

Preparation of oligonucleotide derived nylon beads:

For cyanuric chloride derived oligonucleotides, poly(ethyleneimine) coated nylon beads described above were placed in a volume of 0.1M sodium borate pH 8.3 equal to the volume of the beads at 4° C. The purified cyanuric chloride derived oligonucleotide was then added to the beads, and the mixture was vigorously agitated at ambient temperature (19° to 23° C.) for 60 minutes. The beads were then washed twice with 0.1M sodium borate pH 8.3. Succinic anhydride was then added at a concentration of 10 mg/ml in 90% N-methyl-pyrrolidone, 10% 1M sodium borate pH 8.3 with a volume three times that the volume of the beads. The reaction was allowed to proceed for 1 hour at ambient temperature. The beads were then washed 3 times with 250 ml of 100% N-methyl-pyrrolidone, twice with distilled water, 5 times with 250 ml SDS/FW and then 4 times with 1 liter of distilled water. Beads were stored dry or in 25 mM EDTA. Radioactivity per bead was determined by liquid scintillation counting.

For iodoacetamidobenzoylated oligonucleotides, poly-(ethyleneimine) coated nylon beads described above were placed in a volume of 0.1M sodium borate pH 8.3 equal to the volume of the beads, and iminothiolane was added to a final volume of 5 mg/ml. The beads were allowed to react for 1 hour at ambient temperature and then washed 10 times with 0.1M sodium borate pH 8.3 and 10 mM EDTA at 4° C. The thiolated poly(ethyleneimine) coated nylon beads described above were placed in a volume of 0.1M sodium borate pH 8.3 and 25 mM EDTA equal to the volume of the beads at 4° C. The purified iodoacetamidobenzoylated oligonucleotides were then added to the beads, and the mixture was vigorously agitated at ambient temperature (19° to 23° C.) for 4 hours. The beads were then washed twice with 0.1M sodium borate and 25 mM EDTA and then incubated with a volume three times that of the beads with 10 mg/ml iodoacetamide in a 1:1 v/v ratio N-methyl-pyrrolidone and 0.1M sodium borate pH 8.3. The reaction was allowed to proceed at ambient temperature for 1 hour. The beads were then washed 3 times with 250 ml of 100% N-methyl-pyrrolidone, twice with distilled water, 5 times with 250 ml SDS/FW and then 4 times with 1 liter of distilled water. Beads were stored dry or in 25 mM EDTA. Radioactivity per bead was then determined by liquid scintillation counting.

Preparation of the Membrane Solid Support:

A 16 cm² piece of Nytran™ (Scheicher & Schuell, Keene, N.H.) was incubated with 10 ml of 5 mg/ml iminothiolane in 0.1M sodium borate at pH=8.3 for 30 minutes at ambient temperature. The membrane was washed with 5 changes of the sodium borate buffer described above. The introduced thiol groups were determined using 5,5-dithio-bis(2-nitrobenzoic acid). The derived membrane was then cut into 0.28 cm² discs and washed once with 0.1M sodium borate buffer. IAB-oligonucleotide was prepared as described above and mixed with the membrane discs. 300 membrane discs were submerged in 2 ml of 0.1M sodium borate buffer containing 1.0 mg of IAB-oligonucleotide, and the reaction was allowed to proceed at room temperature with constant agitation for 16 hours in the dark. The discs were then washed sequentially with 0.1M sodium borate, SDS/FW. 1.2 micrograms of Bg5B oligonucleotide was bound per filter disc. The unreacted thiol groups were blocked with 50 mg/ml iodoacetamide in 0.1M sodium borate pH=8.3. The filters were then washed further with sodium borate and SDS/FW.

Lysis of bacteria and hybridization conditions:

$1 \times 10^8$ Cells of Bacteroides gingivalis (Bg) were lysed in 100 μL of lysis solution at 19° C. The cell lysate was then heated in an 65 degree water bath for 10 minutes. Biotinylated probe was added to the lysate solution and to the diluent (GuSCN lysis solution) to a final concentration of 100 ng/mL, and 5 to 8 5-fold serial dilutions were made of the starting lysate. The solutions were incubated with either the derived nylon bead or the Nytran™ (Scheicher & Schuell, Keene, N.H.) that had been covalently immobilized with 0.1 μg of respective oligonucleotide probe (capture probe) for 1 hour at ambient temperature with mild agitation. The solid supports were then washed once with the lysis and hybridization solution, once with FW, and once with SDS/FW. Streptavidin/HRP conjugate was added to a final concentration of 1 microgram/ml (based on streptavidin) in SDS/FW and incubated 10 to 15 minutes at ambient temperature with mild agitation. The beads and filters were then washed three times with SDS/FW and then once with CAP buffer. 4-methoxy-naphthol napthol substrate solution described above was added, and the reaction was allowed to proceed for 15 minutes at ambient temperature. The beads or filters were then quickly washed once with SDS/FW and then once with FW and allowed to air dry in the dark.

Quantitative determination of the extent of hybridization (capture of target nucleic acid) using insoluble substrates for either horseradish peroxidase or alkaline phosphatase:

After the completion of the sandwich assay on the solid support, herein 3/32 inch nylon beads, and the deposition of the insoluble substrate product onto the surface of the bead described above for either HRP or alkaline phosphatase, the quantity of target captured was determined by fluorescence quenching. The beads were dried for 15 to 30 minutes at ambient temperature and then individually placed in a round bottom opaque white microtiter plate (Dynatek Laboratories, Chantilly, Va.). The beads were then read using a fluorometer (Fluoroskan II, Flow Laboratories, McLean, Va.) in which excitation was at 350 nanometers and emmision was at 456 namometers. The beads possessed an intrinsic fluorescence of about 800 relative fluorescence units, and the presence of the colorimetric substrate product effectively quenched the instrinsic fluorescence. The lower the indicated fluorescence correlated with the greater the quantity of captured target nucleic acid.

EXAMPLE 1

Example 1 describes the selective modification and activation of the tethered 5'-amine of oligonucleotides with cyanuric chloride. It is shown that the derivitization of the oligonucleotide occurs only at the tethered amine.

Figure 3B:
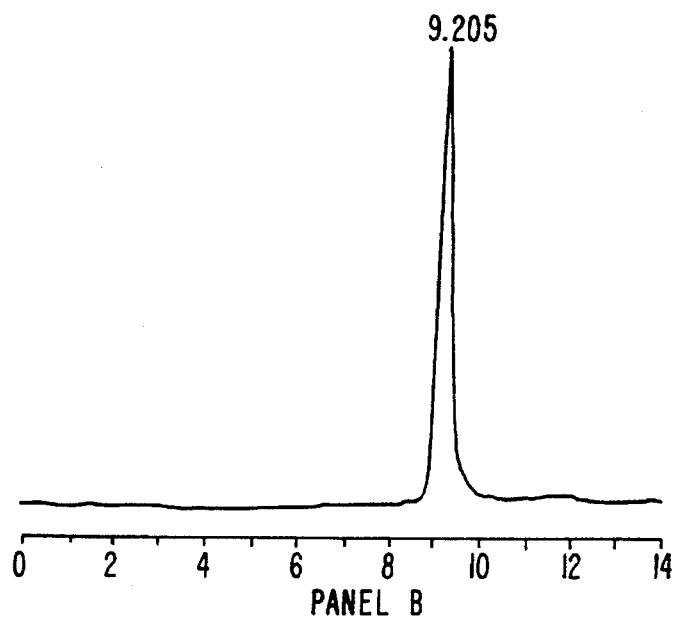
Figure 3C:
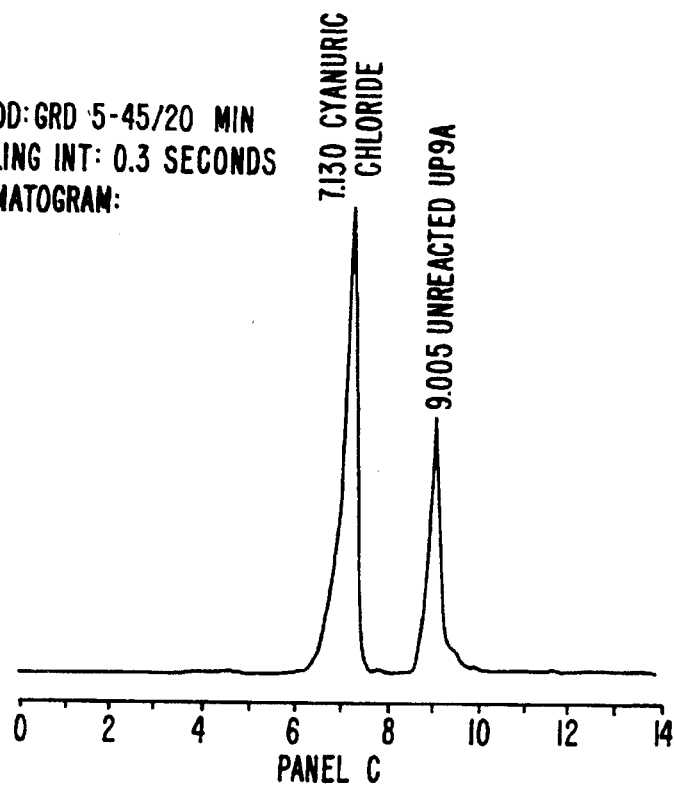
Figure 3D:
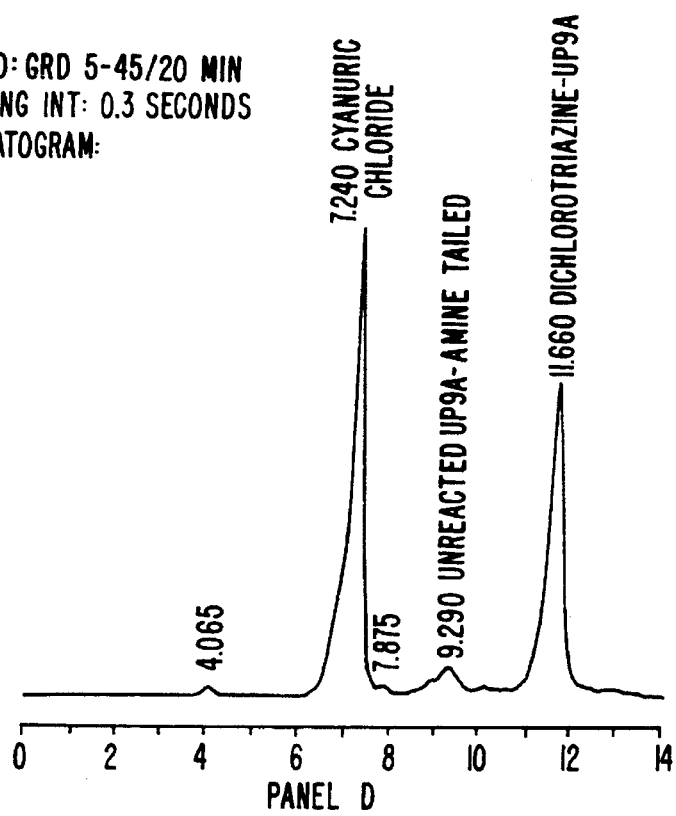

The sequence UP9A, which either possessed a 5'-aminohexyl tail or did not possess a 5'-aminohexyl tail, was compared with respect to reactivity with cyanuric chloride. 50 ug of each type oligonucleotide was reacted in a 400 ul volume containing 0.15M sodium borate pH=8.3, 2 mg/ml cyanuric chloride (from 50 mg/ml freshly prepared stock in 100% acetonitrile). The reaction was allowed to occur at 19° C. for 30 minutes. The reaction mixture was then analyzed by C-18 reverse phase HPLC utilizing a 5 to 45% acetonitrile gradient in TEA. The chromatographs from the respective reaction mixtures and both types of starting oligonucleotide are shown in FIG. 3.

The non-tailed oligonucleotide sequence UP9A is shown in panel A and elutes off the column at 9.025 minutes whereas the amine-tailed oligonucleotide sequence UP9A elutes at 9.205 minutes (panel B). The chromatograph in panel C shows that the non-tailed oligonucleotide sequence UP9A does not react with cyanuric chloride, as the oligonucleotide continues to be eluted at 9.005 minutes. In panel D, the amine-tailed oligonucleotide sequence UP9A reacts almost to completion with cyanuric chloride resulting in a dichlorotriazine derivitive that is eluted at 11.6 minutes, almost 2.5 minutes later than the UP9A amine-tailed starting material. The profiles indicate that only the UP9A sequence possessing the 5'-tethered amine reacted with cyanuric chloride demonstrating that cyanuric chloride reacted selectively with the amine and not with any of the sugars or bases present in the oligonucleotide. Therefore, it was shown that 5'-aminohexyl oligonucleotides are selectively activated with cyanuric chloride, resulting in a probe is immobilized only at the 5'-end onto a solid support.

EXAMPLE 2

This example describes the derivation of nylon beads with several types of diamines and poly(ethyleneimine), and then the subsequent attachment of 4,6-dichlorotriazine oligonucleotides. A comparison of the hybridization properties of the respective beads is also described.

200 bead batches were derived with either hexanediamine, Jeffamine EDR 148, 1,4-phenylenediamine, Jeffamine T3000, or poly(ethyleneimine) using the procedure described above relating to preparation of polymer-coated beads. Each diamine or triamine bead type contained between 200 nmoles to 2 umoles of amine and the poly(ethyleneimine) contained approximately 100 nmoles of amine.

Each bead type was then reacted with 4,6-dichlorotriazine activated oligonucleotide (Bg5 sequence) as described above. The unreacted amines were then blocked with succinnic anhydride as described above and tested in a hybridization assay as described above. The phenylenediamine beads showed no ability to capture target nucleic acid whereas the Jeffamines EDR-148, T-3000, and hexanediamine type beads captured nucleic acid target but at a rate about 25-fold less than that of the poly(ethyleneimine) beads as determined by the fluorescence quenching assay described above. The results are summarized in the table below.

| Bead type: | Lower limit of detection: |
| --- | --- |
| Phenylenediamine | no target detected |
| EDR-148 | $5 \times 10^7$ cells |
| T-3000 | $2.5 \times 10^8$ cells |
| Hexanediamine | $2.5 \times 10^8$ cells |
| Poly(ethyleneimine) | $2 \times 10^6$ cells |

The results indicate that polymer-coated beads were approximately 25-fold more efficient in the capture of target nucleic acid and therefore present the best surface type for covalent immobilization of oligonucleotides and capture of target nucleic acid.

EXAMPLE 3

Example 3 compares the solid supports formed from Nytran™ (Scheicher & Schuell, Keene, N.H.) membranes and nylon beads in a sandwich assay format in which a target nucleic acid sequence is sequestered and then detected using a colorimetric assay format.

3M GnSCN lysis solution was used to lyse $1 \times 10^8$ cells of Actinobacillus actinomycetemcomitans (Aa), Bacteroides gingivalis (Bg), Bacteroides intermedius (Bi), Eikenella corrodens (Ec), Fusobacterium nucleatum (Fn), and Wolinella recta (Wr) in 100 microliter volumes at 19° C. The lysate was then heated to 65° C. for 5 minutes. A biotinylated 24-mer oligonucleotide probe complementary to conserved regions of bacterial 16s rRNA (signal probe) was added to a final concentration of 100 nanograms per ml.

5-fold serial dilutions of the lysates were made using diluents containing the biotinylated signal oligonucleotides and $1 \times 10^8$ total cells of Aa, Bi, Ek, Fn, and Wr. The solutions were then incubated for 30 minutes at ambient temperature with Nytran™ (Scheicher & Schuell, Keene, N.H.) discs or 2 nylon beads that had covalently immobilized 0.1 µg of Bg1 specific oligonucleotide probe (capture probe). The solid supports were washed with SDS/FW at ambient temperature and then incubated with 10 ng/ml of streptavidin/horseradish peroxidase (SA/HRP) conjugate in SDS/FW for 5 minutes at ambient temperature. The solid supports were then washed with SDS/FW, FW, and then the presence of peroxidase was determined by incubating the filter with the HRP substrate solution described above to form an insoluble product.

The results indicated that, in the 30 minute hybridization, $2 \times 10^5$ cells were detected using the nylon beads as solid supports whereas $1 \times 10^6$ cells were detected using Nytran™ (Scheicher & Schuell, Keene, N.H.) solid supports as determined by the fluorescence quenching assay described above. The control in which Aa, Bi, Ek, and Wr cells were present and Bg was absent showed no color, indicating that the capture of Bg was specific. It was also noted that most HRP insoluble substrates faded upon dying on the Nytran™ (Scheicher & Schuell, Keene, N.H.) membranes, whereas no fading occurred on the nylon beads.

EXAMPLE 4

Example 4 compares the solid supports formed from Nytran™ (Scheicher & Schuell, Keene, N.H.)membranes and nylon beads in a sandwich assay format in which a target nucleic acid sequence is sequestered and then detected in a complex biological sample containing whole blood.

3M GnSCN lysis solution was used to lyse $1 \times 10^8$ cells of Bacteroides gingivalis (Bg) spiked into a plaque sample containing visible quantities of blood (approximately 25 microliters packed cell volume) in 250 microliter volume at 19° C. and then split into two equal volumes. The lysate was then heated to 65° C. for 5 minutes. A biotinylated 24-mer oligonucleotide probe complementary to conserved regions of bacterial 16s rRNA (signal probe) was added to a final concentration of 100 nanograms per ml.

5-fold serial dilutions of the lysates were made using diluents in 3M GuSCN lysing and hybridization solution containing the biotinylated signal oligonucleotides and one part in ten of whole blood. The solutions were then incubated for 30 minutes at ambient temperature with a Nytran™ (Scheicher & Schuell, Keene, N.H.) discs or 2 nylon beads that had covalently immobilized 0.1 µg of Bg1 specific oligonucleotide probe (capture probe). The solid supports were then washed with SDS/FW at ambient temperature and incubated with 10 ng/ml of streptavidin/horseradish peroxidase (SA/HRP) conjugate in SDS/FW for 5 minutes at ambient temperature. The solid supports were then washed with SDS/FW, FW, and then the presence of peroxidase was determined by incubating the filter with the HRP substrate solution described above to form an insoluble product.

The results indicated that, in the 30 minute hybridization, $8 \times 10^5$ cells were detected using the nylon beads as solid supports whereas $4 \times 10^6$ cells were detected using Nytran™ (Scheicher & Schuell, Keene, N.H.) solid supports as determined by the fluorescence quenching assay described above. More importantly, the Nytran™ (Scheicher & Schuell, Keene, N.H.) filters were significantly stained with lysed blood products whereas the nylon beads retained their starting color.

EXAMPLE 5

Example 5 compares the solid supports formed from Nytran™ (Scheicher & Schuell, Keene, N.H.) membranes and nylon beads in a sandwich assay format in which a target nucleic acid sequence is sequestered and then detected using a chemiluminescence assay format.

3M GnSCN lysis solution was used to lyse $1 \times 10^8$ cells of Actinobacillus actinomycetemcomitans (Aa), Bacteroides gingivalis (Bg), Bacteroides intermedius (Bi), Eikenella corrodens (Ec), Fusobacterium nucleatum (Fn), and Wolinella recta (Wr) in 100 microliter volumes at 19° C. The lysate was then heated to 65° C. for 5 minutes. A biotinylated 24-mer oligonucleotide probe complementary to conserved regions of bacterial 16s rRNA (signal probe) was added to a final concentration of 100 nanograms per ml.

5-fold serial dilutions of the lysates were made using diluents in 3M GuSCN lysing and hybridization solution containing the biotinylated signal oligonucleotides and $1 \times 10^8$ total cells of Aa, Bi, Ek, Fn, and Wr. The solutions were then incubated for 30 minutes at ambient temperature with Nytran™ (Scheicher & Schuell, Keene, N.H.) discs or 2 nylon beads that had covalently immobilized 0.1 µg of Bg1 specific oligonucleotide probe (capture probe). The solid supports were washed with SDS/FW at ambient temperature following by washing with 0.5% Tween 20, 1 mM MgCl2, 0.01M Tris-HCl pH 8.0 (APB) and then incubated with 0.4 ug/ml of streptavidin/alkaline phosphatase (SA/AP) conjugate in APB for 5 minutes at ambient temperature. The solid supports were washed 5 times with APB, TMNZ, and then the presence of alkaline phosphatase was determined by incubating either the Nytran™ (Scheicher & Schuell, Keene, N.H.) filters or the nylon beads with 200 microliters of Lumigen (from Lumigen, Inc., Detroit, Mich.) in 5 mm ×40 mm polypropylene tubes. The results are shown in the table below.

| Cell number: | Chemiluminescent Signal Nytran ™ solid supports: | Nylon beads: |
|---|---|---|
| $1 \times 10^8$ | off scale | off scale |
| $2 \times 10^7$ | 1600 | off scale |
| $4 \times 10^6$ | 1750 | 1650 |
| $8 \times 10^5$ | 1700 | 680 |
| $1.6 \times 10^5$ | 1600 | 320 |
| $3.2 \times 10^4$ | 1800 | 260 |
| $6.4 \times 10^3$ | 1800 | 210 |
| control | 1700 | 200 |

Therefore, the results indicate that, in the 30 minute hybridization, $3 \times 10^4$ cells were detected using the nylon beads as solid supports whereas only $1 \times 10^8$ cells were detected using the Nytran™ (Scheicher & Schuell, Keene, N.H.) solid supports. This approximately 10,000-fold difference in the lower level of detection of the target was due to the severe background of nonspecific binding of the alkaline phosphatase to the Nytran™ (Scheicher & Schuell, Keene, N.H.) filters. The nylon beads, therefore, allowed the sensitive detection of Bg 16s rRNA using a chemiluminescence based signal system.

EXAMPLE 6

Example 6 demonstrates the nylon solid supports in a sandwich assay format in which a target nucleic acid sequence is sequestered and then detected using a fluorescence-based assay format.

3M GnSCN lysis solution was used to lyse $1 \times 10^8$ cells of Actinobacillus actinomycetemcomitans (Aa), Bacteroides gingivalis (Bg), Bacteroides intermedius (Bi), Eikenella corrodens (Ec), Fusobacterium nucleatum (Fn), and Wolinella recta (Wr) in 100 microliter volumes at 19° C. The lysate was heated to 65° C. for 5 minutes. A biotinylated 24-mer oligonucleotide probe complementary to conserved regions of bacterial 16s rRNA (signal probe) was added to a final concentration of 100 nanograms per ml.

5-fold serial dilutions of the lysates were made using diluents in 3M GuSCN lysing and hybridization solution containing the biotinylated signal oligonucleotides and $1 \times 10^8$ total cells of Aa, Bi, Ek, Fn, and Wr. The solutions were then incubated for 30 minutes at ambient temperature with 2 black nylon beads prepared by The Hoover Group (Sault St. Marie, Mich.) that had covalently immobilized 0.1 µg of Bg1 specific oligonucleotide probe (capture probe). The solid supports were washed with SDS/FW at ambient temperature following by washing with 0.5% Tween 20, 1 mM MgCl2, 0.01M Tris-HCl pH 8.0 (APB) and then incubated with 0.4 ug/ml of streptavidin/alkaline phosphatase (SA/AP) conjugate in APB for 5 minutes at ambient temperature. The solid supports were then washed 5 times with APB, TMNZ, and then the presence of alkaline phosphatase was determined by incubating the nylon beads with 150 microliters of 0.5 mM 4-methyl-umbelliferyl phosphate (4-hydroxymethyl coumarin) in black microtiter well strips (Dynatek, Laboratories, Chantilly, Va.). Incubation was for 30 minutes at 37° C. The plates were then directly read using a Fluoroskan II fluorometer (Flow Laboratories, McLean, Va.) using an excitation wavelength of 360 nm and an emmission wavelength of 456 nm. The results are shown in the table below.

| Cell number: | Fluorescent Signal Nylon beads |
|---|---|
| $1 \times 10^8$ | 1250 |
| $2 \times 10^7$ | 1980 |
| $4 \times 10^6$ | 680 |
| $8 \times 10^5$ | 175 |
| $1.6 \times 10^5$ | 58 |
| $3.2 \times 10^4$ | 26 |
| $6.4 \times 10^3$ | 23 |
| control | 18 |

The results indicate that, in the 30 minute hybridization, $6 \times 10^3$ cells were detected using the nylon beads as solid supports. The nylon beads, therefore, allowed the sensitive detection of Bg 16s rRNA using a fluorescence based signal system.

EXAMPLE 7

Example 7 describes the use of 3/32 inch nylon beads immobilized in a nonporous, plastic card to form a multi-panel detection composition described herein as a dipstick. The dipstick (or indicator card) so formed possesses multiple and distinct sites that allow the specific detection of multiple pathogens in a single sample. In this Example, the specific detection of Bg and Ek is demonstrated.

A set of six identical dipsticks were prepared, in which the general configuration of the dipstick is shown in FIGS. 1 and 2. The five beads, each possessing a different capture oligonucleotide, were placed in the dipstick from left to right in the following order:
1: PA005 (positive control)
2: Aa004 (for the detection of Aa rRNA)
3: Bg002 (for the detection of Bg rRNA)
4: Ek007 (for the detection of Ek rRNA)
5: PA505 (negative control)

Each dipstick was tested in 400 ul lysis and hybridization solution described above containing biotinylated UP9A and UP007 at 500 ng/ml, PA505 at 5 ng/ml, and either:
1) $1 \times 10^8$ Bg cells.
2) $2 \times 10^7$ Bg cells.
3) $1 \times 10^8$ Ek cells.
4) $2 \times 10^7$ Ek cells.
5) $1 \times 10^8$ Bg cells and $1 \times 10^8$ Ek cells.
6) $2 \times 10^8$ Bg cells and $2 \times 10^8$ Ek cells.

The dipsticks were processed sequentially through the following solutions with constant agitation at 2 hertz: 10 minutes in the hybridization solution, 2 minutes in SDS/FW, 5 minutes in SA/HRP conjugate, 2 minutes in SDS/FW, 2 minutes in CAP buffer, and then developed 10 minutes in 4MN substrate solution. The results are described in the following table.

| Bead number: | Solution: | | | | | |
|---|---|---|---|---|---|---|
| | 1 | 2 | 3 | 4 | 5 | 6 |
| 1 | ++ | ++ | ++ | ++ | ++ | ++ |
| 2 | − | − | − | − | − | − |
| 3 | ++ | + | − | − | ++ | + |
| 4 | − | − | ++ | + | ++ | + |
| 5 | − | − | − | − | − | − | wherein ++ indicates strong colorimetric signal, + indicates medium colorimetric signal, − indicates no signal. The results indicate that the dipstick was able to detect specifically the presence of Bg and Ek.

What is claimed is:

1. A dipstick for detecting a member of a ligand pair, comprising a nonporous solid support having at least one depression or at least one perforation and further having attached to the perforation or depression a polymer-coated bead to which a member of a ligand pair is covalently bound.

2. The dipstick of claim 1 wherein the bead is a solid or hollow sphere, a ball, a bearing, a cylinder or a string.

3. The dipstick of claim 1 wherein the polymer-coated bead is nylon and spherical in shape.

4. The dipstick of claim 3 wherein the diameter of the polymer-coated bead is in the range from about 0.01 inch to about 0.5 inch.

5. The dipstick of claim 4 wherein the diameter of the polymer-coated bead is from about 0.06 inch to about 0.09 inch.

6. The dipstick of claim 1 wherein the polymer-coated bead is attached through a pressure fit with a circumference of the perforation or depression.

7. The dipstick of claim 1 wherein the perforations number from about two to about one hundred.

8. The dipstick of claim 1, wherein an oligonucleotide capable of detecting a specific target nucleic acid in a complex biological sample is covalently attached to the polymer coated bead.

9. The dipstick of claim 8 wherein a plurality of oligonucleotides having non-identical nucleic acid sequences is covalently attached to the polymer-coated bead.

10. The dipstick of claim 8 having more than one bead wherein a first polymer-coated bead is covalently attached to a first oligonucleotide having a first nucleic acid sequence and a second polymer-coated bead is covalently attached to a second oligonucleotide having a second nucleic acid sequence that is non-identical to the first nucleic acid sequence.

11. The dipstick of claim 1 wherein the first oligonucleotide is capable of detecting a specific first target nucleic acid in a complex biological sample and the second oligonucleotide is capable of detecting a specific second target nucleic acid in a complex biological sample.

* * * * *